United States Patent
Zhang et al.

(10) Patent No.: US 11,802,056 B2
(45) Date of Patent: Oct. 31, 2023

(54) METHODS FOR WATER ENVIRONMENT MULTI-INTERFACE GOVERNANCE AND RESTORATION IN RIVERS AND LAKES

(71) Applicant: CHINESE RESEARCH ACADEMY OF ENVIRONMENTAL SCIENCES, Beijing (CN)

(72) Inventors: Lieyu Zhang, Beijing (CN); Guowen Li, Beijing (CN); Lulu Che, Beijing (CN); Xiaoguang Li, Beijing (CN); Caole Li, Beijing (CN); Jiaqian Li, Beijing (CN); Chen Zhao, Beijing (CN); Wei Li, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 90 days.

(21) Appl. No.: 17/239,632

(22) Filed: Apr. 25, 2021

(65) Prior Publication Data
US 2022/0073369 A1 Mar. 10, 2022

(30) Foreign Application Priority Data
Sep. 7, 2020 (CN) .......................... 202010926483.3

(51) Int. Cl.
*C02F 3/32* (2023.01)
*C02F 1/00* (2023.01)
(Continued)

(52) U.S. Cl.
CPC .............. *C02F 1/006* (2013.01); *C02F 3/006* (2013.01); *C02F 3/32* (2013.01); *C02F 7/00* (2013.01);
(Continued)

(58) Field of Classification Search
CPC .. C02F 1/008; C02F 3/006; C02F 3/32; C02F 3/327; C02F 7/00; C02F 2103/007
(Continued)

(56) References Cited

U.S. PATENT DOCUMENTS 4,732,682 A * 3/1988 Rymal .................... C02F 3/207
   210/242.2
5,387,343 A * 2/1995 Iwai ........................ C02F 3/34
   210/747.5
(Continued)

FOREIGN PATENT DOCUMENTS

CN     1769198 A    5/2006
CN   105645563 A    6/2016
(Continued)

OTHER PUBLICATIONS

Machine translation of CN 105645563, Jun. 2016 (Year: 2016).*
(Continued)

*Primary Examiner* — Christopher Upton
(74) *Attorney, Agent, or Firm* — Jaffery Watson Mendonsa & Hamilton LLP

(57) ABSTRACT

The present disclosure relates to water environment governance technology, and particularly discloses an urban river/lake water environment multi-interface governance and restoration method. The method is a multi-interface coordinated governance and restoration method based on "control for bottom, regulation for middle and governance for top", including: "control for bottom"—controlling the emission of sediment nutritive salts and the dormancy and recovery of algae; "regulation for middle"—regulating primary productivity in a water body to inhibit the recovery of the algae; and "governance for top"—reducing nitrogen and phosphorus nutrients of an air-water interface to control the reproduction and growth of the algae. In the present disclosure, the water body governance and restoration technology based on interface coordination can effectively inhibit the outbreak of cyanobacteria and avoid extreme conditions in the ecosystem.

7 Claims, 4 Drawing Sheets

(51) Int. Cl.
  *C02F 7/00* (2006.01)
  *G01N 33/28* (2006.01)
  *C02F 3/00* (2023.01)
  *C02F 103/00* (2006.01)
(52) U.S. Cl.
  CPC .... *G01N 33/2823* (2013.01); *C02F 2001/007* (2013.01); *C02F 2103/007* (2013.01)
(58) Field of Classification Search
  USPC ............. 210/602, 614, 747.5, 747.6, 170.09, 210/170.11, 242.2
  See application file for complete search history.

(56) References Cited

U.S. PATENT DOCUMENTS

| | | | | |
|---|---|---|---|---|
| 5,549,828 | A * | 8/1996 | Ehrlich | C02F 3/327 210/602 |
| 7,758,752 | B2 * | 7/2010 | Pan | C02F 1/288 210/602 |
| 11,420,889 | B2 * | 8/2022 | Gu | C02F 3/327 |
| 2002/0104807 | A1 * | 8/2002 | Keeton, Jr. | C02F 7/00 210/747.5 |
| 2005/0045556 | A1 * | 3/2005 | Kryzak | C02F 3/327 210/602 |
| 2016/0376181 | A1 * | 12/2016 | An | C02F 3/327 210/170.1 |
| 2021/0389293 | A1 * | 12/2021 | Zhang | G06V 10/762 |
| 2022/0071113 | A1 * | 3/2022 | Li | A01G 33/00 |
| 2022/0073382 | A1 * | 3/2022 | Zhao | C02F 11/15 |

FOREIGN PATENT DOCUMENTS

| | | |
|---|---|---|
| CN | 109879436 A | 6/2019 |
| CN | 211226561 U | 8/2020 |
| KR | 20150016770 A | 2/2015 |

OTHER PUBLICATIONS

Machine translation of CN 109879436, Jun. 2019 (Year: 2019).*
Machine translation of CN 1769198, May 2006 (Year: 2006).*
Machine translation of CN 211226561, Aug. 2020 (Year: 2020).*
Machine translation of KR 20150016770, Feb. 2015 (Year: 2015).*
Chinese Application No. 202010926483.3, First Office Action dated May 27, 2021, 11 pages.

* cited by examiner

METHODS FOR WATER ENVIRONMENT MULTI-INTERFACE GOVERNANCE AND RESTORATION IN RIVERS AND LAKES

CROSS REFERENCE TO RELATED APPLICATION

This application claims the benefit of Chinese Patent Application No. 2020109264833, filed Sep. 7, 2020, which is hereby incorporated by reference herein in its entirety.

TECHNICAL FIELD

The present disclosure relates to water environment governance technology, in particular to an urban river/lake water environment multi-interface governance and restoration method.

BACKGROUND

With the acceleration of economic development and urbanization, the problem of urban water shortage is particularly prominent. At present, a considerable part of cities is short of water resources, the scope of urban water supply is increasingly expanding, and the degree of water shortage is getting worse. It is predicted that the water resource crisis of the century will rank first among all resource crises in the world. Therefore, it is particularly important to realize the recycling of sewage, alleviate the contradiction between supply and demand of water resources, and promote the sustainable development of the national economy.

Reclaimed water refers to water that can be used beneficially after wastewater or rainwater has been properly treated to reach certain water quality indexes and meet certain usage requirements. Compared with seawater desalination and transbasin diversion, reclaimed water has obvious advantages. From an economic point of view, the cost of reclaimed water is the lowest. From an environmental point of view, sewage reclamation helps to improve the ecological environment and realize a virtuous cycle of water ecology.

Rivers and lakes are an important part of the urban landscape and ecological environment. The water replenishment of rivers and lakes in Beijing mainly relies on reclaimed water. However, due to the degradation of urban river/lake ecosystems and weak self-regulation capability, the high nitrogen load input of reclaimed water can easily cause cyanobacterial blooms and other environmental risks. The air-water interface and the sediment-water interface are the key areas for water pollutant input, material circulation and transformation, and the physicochemical environment of the interface is easily disturbed by the outside. Especially under sudden environmental conditions such as rainwater and sewage overflow, the interface will be disordered, and the ecosystem is prone to extreme conditions or even collapse, which seriously affects the city image and the urban ecological environment, and directly endangers the safety of urban drinking water sources and the health of residents. Therefore, water body governance and restoration technology based on interface coordination is needed to provide technical support for the continuous improvement of the water ecological environment quality of the large cities suffering from water shortage in the north of China.

SUMMARY

In order to solve the problems in the prior art, an objective of the present disclosure is to provide a river/lake water environment multi-interface governance and restoration method. The method provided by the present disclosure can effectively eliminate the problem of eutrophication of water bodies replenished with reclaimed water sources in large, medium and small cities, ecologically restore seriously polluted water bodies, reduce the pollution load of downstream rivers, improve the functions of the river ecosystem and beautify the surrounding landscape environment.

The method of the present disclosure is actually a multi-interface coordinated governance and restoration method based on "control for bottom, regulation for middle and governance for top", including: "control for bottom"—controlling the emission of sediment nutritive salts and the dormancy and recovery of algae; "regulation for middle"—regulating primary productivity in a water body to inhibit the recovery of the algae; and "governance for top"—reducing nitrogen and phosphorus nutrients of an air-water interface to control the reproduction and growth of the algae.

The method is specifically as follows:

(1) "Control for bottom": Technology of performing accurate locating and in-situ treatment on pollutants at a sediment-water interface is adopted to solve the problems of large dredging amount of urban river/lake sediment, difficulty in piling and high treatment cost in the subsequent treatment process and the like, thereby effectively controlling the emission of the sediment nutritive salts. Part of dormant algae are removed from the sediment-water interface to destroy the dormant microenvironment for the algae in winter, significantly reduce the number of the dormant algae and lower the survival rate of the algae at the sediment-water interface in winter, thereby effectively controlling the dormancy and recovery of the algae at the sediment-water interface.

(2) "Regulation for middle": A modified clay molecular sieve ecological base is prepared to establish a good growth environment for grass seeds of submerged plants. A modified clay molecular sieve in the ecological base is a silicate compound, its porous structure is conducive to the growth of phosphorus-accumulating bacteria, and at the same time, the modified clay molecular sieve improves the water-deposit microenvironment and increases the dissolved oxygen concentration in the microenvironment. Ferrous ions in deposit are oxidized to ferric iron, thereby further inhibiting the emission of phosphorus in the deposit. In the meanwhile, the porous structure of the modified clay molecular sieve is combined with the growth of the submerged plants, thereby significantly reducing the disturbance at a water-deposit interface, and inhibiting the emission of the deposit cyanobacteria to the water body.

After a submerged vegetation system is established, the vigorous growth of the submerged plants can fix the sediment and decelerate the nutritive salt cycle at the sediment-water interface. At the same time, under the coordination of phenolic acid and fatty acid allelochemicals such as N-phenyl-2-naphthylamine, methyl dehydroabietate and ethyl dehydroabietate secreted by the submerged plants, cyanobacteria cells are oxidized in response to oxidative stress, thereby destroying the lipid proteins and nucleic acids of cyanobacteria cells and affecting the metabolism of cyanobacteria. In combination with the modified clay molecular sieve ecological base improving the aerobic microenvironment of the water-deposit interface, the objective of inhibiting recovery, growth and reproduction of cyanobacteria is achieved.

(3) "Governance for top": A micropower biological-ecological coupled purification system is used to improve hydrodynamic conditions of the air-water interface and the water body, enhance the nitrogen and phosphorus removal capabilities and solve the problems of insufficient hydrodynamic force at the air-water interface of small rivers and lakes, difficulty in enrichment of microorganisms, and low purification efficiency.

The micropower biological-ecological coupled purification system includes a solar micro-aeration cycle device, a composite high-efficiency microbial agent, a carrier filler and aquatic plants cultivated thereon.

More specifically, in the "control for bottom" method: high-throughput sequencing technology and pollutant source apportionment technology are firstly used to perform accurate locating on sediment to be governed, and then electrodialysis-vacuum negative pressure dewatering technology is used to perform in-situ dewatering treatment on the sediment to be governed.

Further, in the "control for bottom" method, a high-throughput sequencing means in molecular biology is used to analyze abundance of alkaline phosphatase phoD functional flora in the sediment, and the position of the sediment to be governed is determined according to an analysis result.

Furthermore, in the "control for bottom" method, the pollutant source apportionment technology is used to measure emission flux of bioavailable phosphorus of the sediment at different depths at the determined position of the sediment to be governed, and a depth of the sediment to be governed is determined according to a measurement result.

Further, in the "control for bottom" method, the method for performing in-situ dewatering treatment on the sediment includes: using nitrate to adjust pH of a water body of an area to be governed to 7.5-8.3, and changing dominant flora in the sediment; and placing the sediment to be governed in a low-voltage high-current electric field, and performing dewatering treatment on the sediment under vacuum negative pressure conditions.

Preferably, after the nitrate is added, low-oxygen aeration treatment is performed on the water body.

An oxygen aeration amount of the low-oxygen aeration is 30-60 mg/L, preferably 50 mg/L.

Preferably, the low-voltage high-current electric field is an electric field with a voltage of 10-12 V and a current of 8-10 A.

More specifically, the "control for bottom" method includes the following steps:

(1) taking sediment samples at different positions of the sediment-water interface in a river/lake water area to be governed, extracting microbial DNA in the samples, performing 16sRNA high-throughput sequencing analysis to obtain abundance of alkaline phosphatase phoD functional flora in the sediment samples at the different positions, and determining the sampling position of the sediment sample with the abundance of alkaline phosphatase phoD functional flora of greater than 25% as the position of the sediment to be governed;

(2) measuring emission flux of bioavailable phosphorus of the sediment at different depths at the determined position of the sediment to be governed in step (1), and determining a depth range where the emission flux is greater than 0.6 mg/L as the depth of the sediment to be governed; and (3) performing dewatering treatment on the sediment to be governed on the basis of the determined position and depth of the sediment to be governed in step (1) and step (2):

firstly using nitrate to adjust pH of a water body of an area to be governed to 7.5-8.3, and changing dominant flora in the sediment in cooperation with low-oxygen aeration; and then placing the sediment to be governed in a low-voltage high-current electric field, and performing dewatering treatment on the sediment under vacuum negative pressure conditions.

By adding the nitrate to the sediment and adopting the low-oxygen aeration manner, the water body can present a facultative aerobic state. With the participation of denitrifying bacteria, organic matter in the water body can be quickly consumed in a short time. At the same time, due to the reproduction of the denitrifying bacteria, the denitrifying bacteria can form a competition mechanism with sulfobacteria to inhibit the growth of the sulfobacteria, thereby inhibiting the production of hydrogen sulfide. The nitrate is sodium nitrate and/or potassium nitrate.

The denitrifying bacteria include *Pseudomonas denitrificans, Thiobacillus denitrificans, Micrococcus denitrificans* and the like.

Furthermore, the low-voltage high-current electric field is formed by the following method: positive and negative electrodes are placed oppositely at an edge of the sediment to be governed and inserted into the sediment, and a voltage of 12 V and a current of 10 A are applied to form the low-voltage high-current electric field.

For the electrode, a carbon fiber bundle used as a conductive current collector and conductive carbon black and graphite powder used as conductive materials are blended with plastic and thermoformed to obtain an electrode material.

Preferably, a depth at which the positive and negative electrodes are inserted into the sediment is ⅔ of a length of the electrode.

Furthermore, the sediment and its surrounding water body (sediment-water mixture) are sucked in by a vacuum negative pressure device through a water pipe and then are dewatered. Due to the addition of the nitrate and the low-oxygen aeration treatment, the sediment to be governed has been transformed from a sulfur-based autotrophic denitrification process to an autotrophic-heterotrophic denitrification coupled process. At the same time, under the action of the low-voltage high-current electric field, heavy metals and positively charged water molecules move to the cathode under the action of the electric field, thereby realizing sludge dewatering and coordinated removal of heavy metals. The sediment treatment method of step (3) can increase the dewatering speed of the sediment to be governed, reduce the water content of viscous sediment with poor permeability to about 50%, and reduce the volume of the sediment by 20-30%.

In the present disclosure, the term "alkaline phosphatase phoD functional flora" refers to functional flora with a function of hydrolyzing organic phosphorus, mainly including bacteria of the genera *Limnohabitans, Pirellula, Plesiocystis* and the like. The alkaline phosphatase phoD functional flora can remove phosphate groups on molecules such as nucleotides, proteins and alkaloids to perform dephosphorylation, and is most effective in alkaline environments.

The high-throughput sequencing technology and the pollutant source apportionment technology adopted in the present disclosure are conventional technical means in the art, which are only exemplified in specific implementations of the present disclosure and are not otherwise limited.

More specifically, the "regulation for middle" method includes the following steps:

(1) cultivating emerging plants in a water area to be governed to improve anti-wind wave and anti-water flow capabilities of the water area to be governed and establish a relatively stable microenvironment; and (2) using a modified clay molecular sieve, phosphorus-accumulating bacteria, grass seeds of submerged plants and silty clay to prepare a modified clay molecular sieve ecological base, and uniformly adding the modified clay molecular sieve ecological base to the water body of the area to be governed.

Further, the grass seeds of the submerged plants are grass seeds of *Potamogeton crispus* and *Vallisneria spiralis*. Considering the effects of light and water body turbidity, the grass seed mixing ratio is set to 2:1.

Further, the preparation method of the modified clay molecular sieve ecological base includes: weighing the modified clay molecular sieve and the silty clay in a ratio of 1:1, adding the grass seeds and the phosphorus-accumulating bacteria, and uniformly mixing the mixture.

The addition amount of the grass seeds is 40-60 seeds/$m^2$, that is, based on the unit area covered by the modified clay molecular sieve ecological base added to water, 40-60 grass seeds are added to the modified clay molecular sieve ecological base covering 1 square meter of water area. The addition amount of the phosphorus-accumulating bacteria is 50% (v/v) relative to the total volume of the modified clay molecular sieve and the silty clay.

A preparation method of the modified clay molecular sieve includes: selecting water body sediment and shore clay, and using the clay after drying, grinding and sieving, or purchasing a professional clay sewage treatment agent; and adding the treated clay to a chitosan solution to form a slurry, or spraying the chitosan solution on the constantly stirred clay (referring to CN 102502969A), where the amount of the chitosan is 1%-1.5% (w/w) of the clay.

The phosphorus-accumulating bacteria are commercially available products, for example, anaerobic phosphorus-accumulating bacteria that can be purchased from Yangzhou Haicheng Biotechnology Co., Ltd. The product is in the form of bacterial powder, and the content of the phosphorus-accumulating bacteria is up to 95% or above.

Further, the first addition amount of the modified clay molecular sieve ecological base is not less than 500 g/$m^2$.

The modified clay molecular sieve ecological base is supplementally added every 5-7 days after the first addition, and the supplemental addition amount is 50% of the first addition amount.

Furthermore, the cultivation density of the emerging plants is 5-6 plants/$m^2$.

The emerging plants are respectively selected from one or more of *Pontederia cordata, Typha orientalis* and *Canna indica* and one or more of native organisms.

The cultivating time of the emerging plants needs to be before the recovery of the cyanobacteria.

Preferably, the method is applicable to a water area with a water depth of less than 3 meters and a wind speed of less than 8 m/s.

The phosphorus-accumulating bacteria of the present disclosure, also called phosphorus uptake bacteria and phosphorus-removing bacteria, are a special type of bacteria in the traditional activated sludge technique. The phosphorus-accumulating bacteria can inhale excessive amounts of phosphorus in sewage in an aerobic state to make the phosphorus content in the phosphorus-accumulating bacteria be several times higher than that in ordinary bacteria. This type of bacteria is widely used for biological phosphorus removal.

More specifically, the "governance for top" method includes:
(1) using a polyester fiber matrix material as a carrier filler, cultivating emerging plants and submerged plants on the carrier filler, and using the solar micro-aeration cycle device to aerate the water body to control the dissolved oxygen concentration of the water body to be not less than 3.0 mg/L; and
(2) after plant roots of the aquatic plants are developed, adding the composite high-efficiency microbial agent to the filler and the plant roots.

Further, the solar micro-aeration cycle device includes solar panels and a flowing water reaeration device. The solar panels are located at an upper part of the device, and used to absorb solar energy and convert the solar energy into electric energy to supply energy to the flowing water reaeration device at a lower part at an output power of 100 w-20 kw. The flowing water reaeration device is located at the lower part of the device, provided with an impeller, and driven by the electric energy of the solar panels to promote the cycle of the water body and drive the micropower biological-ecological coupled purification system to move. The cycle flux is 100-50000 $m^3$/h, and the flowing water distance or action range is 100-3500 m.

Further, the composite high-efficiency microbial agent is mainly extracted and domesticated from nature, and has the feature of efficiently decomposing organic matter, ammonia nitrogen, total nitrogen and other pollutants.

Further, in the present disclosure, the polyester fiber matrix material having a specific surface area of 1:1000 and a porosity of 97% is used as the carrier filler, thereby providing a carrier for adherence of microorganisms and cultivation of the emerging plants and the submerged plants. In addition, the carrier filler can promote the root division and growth of the aquatic plants and the seed drop and growth of wild plants, enhance the viability of plants and expand the range of the plant roots.

Further, the aquatic plants cultivated on the carrier filler include the emerging plants and the submerged plants. The emergent plants are mainly plants with developed and dense roots such as *Pontederia cordata, Typha orientalis* and *Acorus calamus*, and species where the project is located are preferred. The submerged plants are preferably *Elodea nuttallii* in cold seasons and *Vallisneria spiralis* in warm seasons, with a cultivation density of 40-60 plants/$m^2$.

In the method "control for bottom" of the present disclosure, the high-throughput sequencing technology and the pollutant source apportionment technology are used to perform accurate locating on the sediment to be governed, and then the electrodialysis-vacuum negative pressure dewatering technology is used to perform in-situ dewatering treatment on the sediment to be governed, thereby realizing accurate governance on the river/lake water environment with the minimum desilting amount. In further cooperation with the application of microbial reagents, the microbial flora environment of the sediment-water interface is regulated, thereby realizing transformation of the sediment from the sulfur-based autotrophic denitrification process to the autotrophic-heterotrophic denitrification coupled process, and increasing the dewatering speed of the sediment. In combination with the electrodialysis-vacuum negative pressure dewatering technology disclosure, the water content of the sediment can be reduced to about 50%, the volume of the sediment can be reduced by 20-30%, and the dewatering cost and the subsequent treatment cost of electrodynamic sludge dewatering can be reduced by 30% or above and about 40% respectively. While increasing the dewatering rate, the operating cost and subsequent treatment cost are reduced.

In the method "regulation for middle" of the present disclosure, the emerging plants are cultivated in the water area to be governed to improve anti-wind wave and anti-water flow capabilities of the water area to be governed and establish the relatively stable microenvironment; and the modified clay molecular sieve, the phosphorus-accumulating bacteria, the grass seeds of the submerged plants and the silty clay are used to prepare the modified clay molecular sieve ecological base, and the modified clay molecular sieve ecological base is uniformly added to the water body of the area to be governed to inhibit the emission of phosphorus in the deposit and reduce disturbance, so that the cyanobacteria in the deposit is fixed, thereby improving the oxygen-deficient microenvironment of the sediment-water interface and achieving the objective of inhibiting growth of cyanobacteria. The germination rate of the grass seeds of the submerged plants can be increased to 80% or above, the field planting survival rate of the aquatic plants is increased by 40% as compared with the traditional method, the emission of sediment pollution is effectively controlled, the submerged plant ecology improves and regulates the primary productivity of the water body, and the allelopathy of plants further restricts the recovery, growth and reproduction of cyanobacteria. In addition, the establishment of the submerged vegetation system provides a habitat for aquatic animals, forming a healthy water ecosystem with an integral structure.

In the method "governance for top" of the present disclosure, the micropower biological-ecological coupled purification system that integrates the polymer composite fiber matrix material (carrier filler), the high-efficiency rhizosphere microorganisms and the solar micro-aeration cycle device is used to enhance the dissolved oxygen level of each interface, and enhance and activate the biological reactions in the air-water interface and the water body. The high-efficiency microorganisms in the air-water interface and the water body adhere and grow on filler pores and the plant roots to form a high-efficiency biofilm, which has a significant rhizosphere effect and improves the contact efficiency between the water body and the microbial film. The special structure and the biofilm of the roots formed between the filler pores and plant roots form a microscopic aerobic-anaerobic continuous alternating environment under the gradient of the dissolved oxygen, thereby providing good conditions for nitration and denitrification reactions. At the same time, the nitrogen, phosphorus and heavy metals are adsorbed by the microbial film, and assimilated by plants. The biomass of the aquatic plants such as *Pontederia cordata, Typha orientalis* and *Acorus calamus* is increasing year by year, so that the allelopathy of the aquatic plants is enhanced, and an underwater microbial system is gradually strengthened, thereby forming an overwater and underwater three-dimensional habitat platform.

The raw materials or reagents involved in the present disclosure are all common commercial products, and the operations involved are conventional operations in the art unless otherwise specified.

Based on conforming to common knowledge in the art, the above preferred conditions can be combined with each other to obtain specific implementations.

The Present Disclosure has the Following Beneficial Effects:

In the method of the present disclosure, in view of the earth and chemical cycle process of biogenic elements based on air-water-sediment "three phases and two interfaces" of reclaimed water as well as the bloom and extinction mechanism of cyanobacteria, an air-water-sediment multi-interface coordinated restoration theory is formed.

Under high nitrogen load conditions, the significant increase in the activity of a photosynthetic system II of cyanobacteria at the air-water interface and the continuous emission of bioavailable phosphorus at the sediment-water interface are the main reasons for the outbreak of cyanobacterial blooms. The water environment interface restoration theory formed based on the bloom and extinction mechanism of cyanobacteria at the air-water-sediment interface includes:

(1) At the sediment-water interface, the emission of bioavailable phosphorus in the deposit under high nitrogen load conditions is the main driving force for growth of cyanobacteria. Through the enzymatic labeling method in biology, it is found that algae have their own strategies for using phosphorus. Secreting extracellular phosphatase to hydrolyze organic phosphorus is an important mechanism for some algae to supplement the phosphorus nutrient. Due to the rich Fe—P content in the eutrophic river/lake deposit, the endogenously emitted phosphorus in the deposit and the nitrogen supplied by the reclaimed water are coupled to accelerate the formation of the cyanobacterial blooms, and the physical disturbance of the sediment-water interface and the resuspension of deposit particles are the most important driving forces for the migration and transformation of a phosphorus interface in the deposit. (2) The absorption and transformation of phosphorus by the submerged plants is the main way of phosphorus cycle in the deposit. The roots of the submerged plants have the function of fixing the deposit, thereby avoiding the physical disturbance of the sediment-water interface and the resuspension of the deposit particles, and effectively controlling the migration of the phosphorus in the deposit from the sediment-water interface to the water body. In the competition of phosphorus between grass and algae in the sediment, the submerged plants have obvious competitive advantages. (3) The coordination of the nitrogen and phosphorus at the air-water interface accelerates the exponential growth of cyanobacteria. A suitable temperature, an environment convenient for receiving light, and frequent exchange of $CO_2$ in the atmosphere and water bodies significantly promote the carbon assimilation rate in the photosynthesis of cyanobacteria, and increase the activity of the photosynthetic system II, thereby enhancing the photosynthesis rate and efficiency of cyanobacteria, and facilitating rapid growth of cyanobacteria biomass. The concentration of $CO_2$ dissolved in the water body has a significant positive correlation with the photosynthesis rate. The wind flow disturbance at the air-water interface and the alkaline water body facilitates the migration of carbon dioxide in the air to the water phase. The main mode of occurrence of carbon in alkaline water is [$HCO3^-$], which can be absorbed and utilized by the unique carbon dioxide concentration mechanism (CCM) of cyanobacteria, thereby further promoting the growth of cyanobacteria biomass.

The driving mechanism of the three-stage process of "dormancy, recovery, and exponential growth and accumulation" formed by the total nitrogen to the cyanobacteria blooms is as follows: in the river/lake water body replenished with reclaimed water, the growth and bloom formation of cyanobacteria can be divided into three stages: dormancy at the sediment-water interface, recovery in the water body, and exponential growth and accumulation at the air-water interface. (1) In the dormant stage (December to March next year), the high nitrogen load enhances the overwintering viability of the cyanobacteria in the deposit. Under high nitrogen conditions, sufficient nutrients at the sediment-water interface provide a good habitat for the dormancy of the cyanobacteria deposited at the bottom and enhance their overwintering viability in the deposit phase. (2) In the recovery stage (March to April), the high nitrogen concentration promotes the recovery of algae cells, so the recovery period is significantly earlier than that under low nitrogen conditions. The recovery occurs at the sediment-water interface and is positively correlated with the effective accumulated temperature. Under high nutrient load conditions, the temperature threshold for the recovery of bloom-forming cyanobacteria in rivers and lakes is much lower than that in other rivers and lakes. The abundant bioavailable phosphorus (BAP) in the deposit is more likely to induce the synthesis of $Na^+K^+$-ATPase and $Ca^{2+}Mg^{2+}$-ATPase in an environment lacking competition from submerged plants, thereby promoting the restoration of photosynthetic activity of the cyanobacteria and stimulating the recovery and rapid growth of the algae cells, so the recovery period is significantly earlier than that under low nitrogen conditions. (3) In the exponential growth and accumulation stage, the activity of the photosynthetic system II of the cyanobacteria at the air-water interface is significantly enhanced under high nitrogen load conditions, thereby promoting the rapid and exponential growth of the cyanobacteria. The high nitrogen load can enhance the transcription level and expression level of various physiologically active enzyme genes in cyanobacteria cells, accelerate synthesis of photosynthesis related proteins, and significantly enhance the stability of the pigment spatial structure, the electron transport rate in photosynthesis and the carbon assimilation efficiency in photosynthesis, so that the absorption and utilization rate of light energy by cyanobacteria cells is greatly increased, and the capability to resist light inhibition is enhanced. In addition, due to the lack of inhibition of photosynthetic bacteria and large aquatic plants, driven by more favorable photosynthetic conditions, the air-water interface is conducive to exponential growth and reproduction and rapid accumulation of the bloom-dominant species Microcystis (cyanobacteria) belonging to K-strategists, forming cyanobacterial blooms.

DETAILED DESCRIPTION

In order to understand the above objectives, features and advantages of the present disclosure more clearly, the solution of the present disclosure will be further described below. It should be noted that in the case of no conflict, the embodiments in the present disclosure and the features in the embodiments may be combined with each other.

Many specific details are explained in the following description in order to fully understand the present disclosure, but the present disclosure may also be implemented in other manners different from those described here. Obviously, the embodiments in the specification are only a part of the embodiments of the present disclosure, rather than all the embodiments.

The preferred implementations of the present disclosure will be described in detail below in conjunction with embodiments. It should be understood that the following embodiments are given for illustrative purposes only, and are not intended to limit the scope of the present disclosure. Those skilled in the art can make various modifications and substitutions to the present disclosure without departing from the objective and spirit of the present disclosure.

The experimental methods used in the following embodiments are conventional methods unless otherwise specified.

The materials, reagents and the like used in the following embodiments are commercially available unless otherwise specified.

Embodiment 1

In this embodiment, a heavily polluted river (the water surface had a length of about 20 m, a width of about 2 m and a total area of 40 m$^2$, a river section for disposing equipment was at the shore, the water depth was 1-2 m, the water quality was inferior to the water quality standard Class V according to the Environmental Quality Standards for Surface Water, and the dissolved oxygen was less than 2.0 mg/L) was taken as the governance and restoration object.

Figure 1:
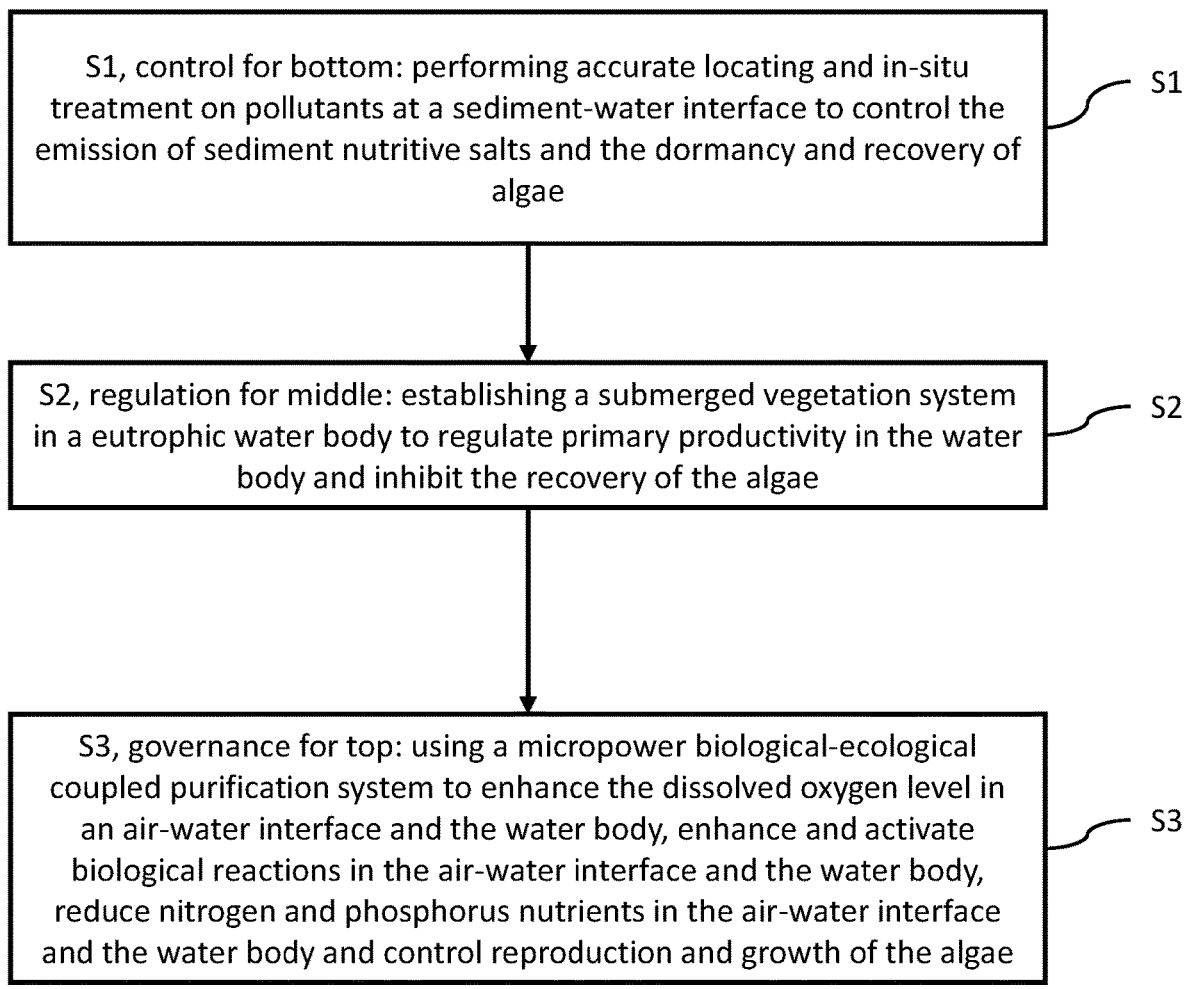
FIG. 1 is a flow chart illustrating a governance and restoration method in accordance with some embodiments of the present disclosure.
Figure 2:
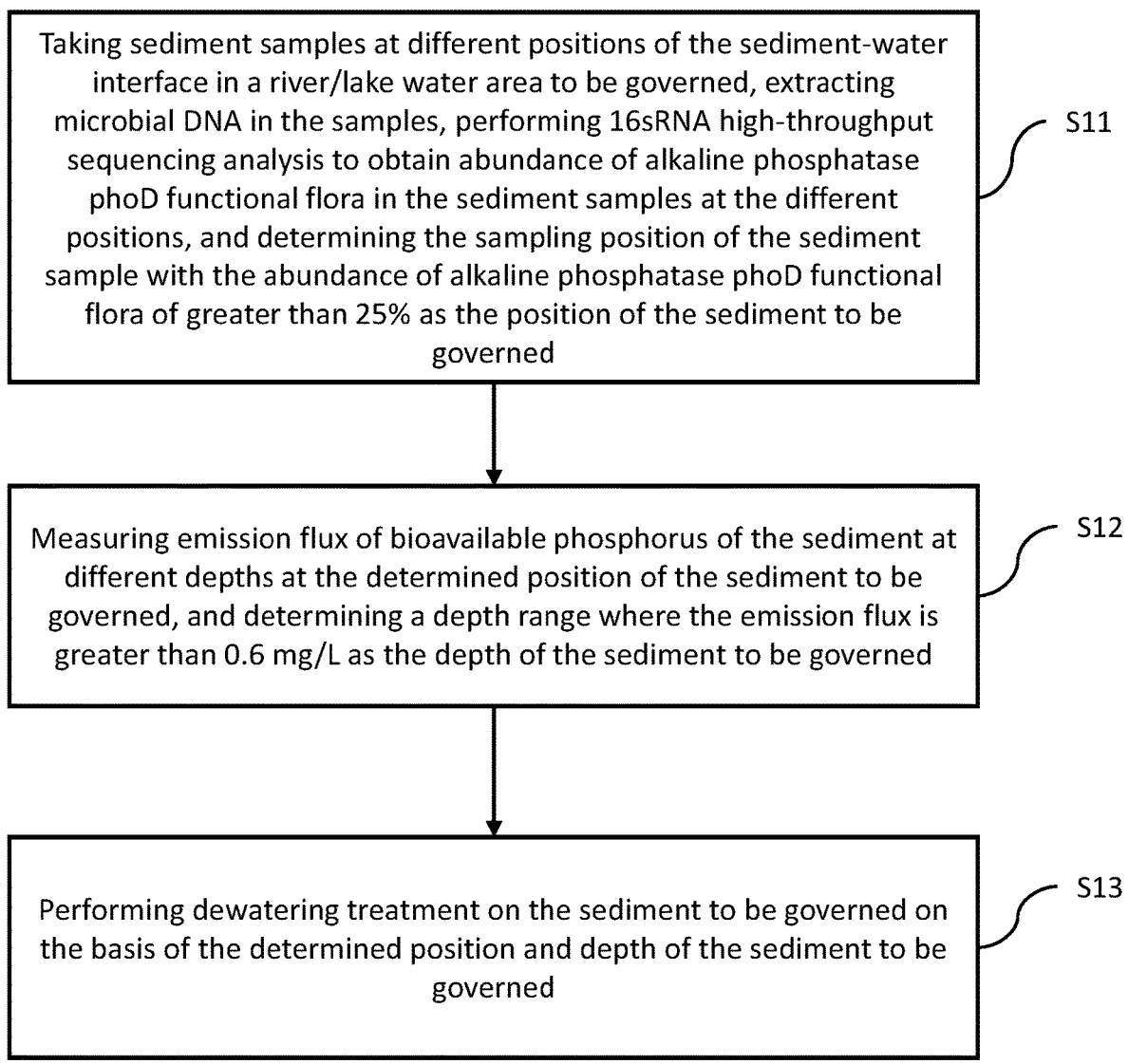
FIG. 2 is a flow chart illustrating an example method for performing S1 of FIG. 1.

As shown in FIGS. 1 and 2, the governance and restoration method specifically included the following steps:

S1, accurate locating and in-situ treatment were performed on pollutants at a sediment-water interface to control the emission of sediment nutritive salts and the dormancy and recovery of algae.

As shown in FIG. 2, at step S11, sediment samples were taken at different positions of the sediment-water interface in a river/lake water area to be governed, microbial DNA was extracted from the samples, 16sRNA high-throughput sequencing analysis was performed to obtain abundance of alkaline phosphatase phoD functional flora in the sediment samples at the different positions, and the sampling position of the sediment sample with the abundance of alkaline phosphatase phoD functional flora of greater than 25% was determined as the position of the sediment to be governed.

As shown in FIG. 2, at step S12, emission flux of bioavailable phosphorus of the sediment at different depths was measured at the determined position of the sediment to be governed in step (1), and a depth range where the emission flux was greater than 0.6 mg/L was determined as the depth of the sediment to be governed.

The emission flux of bioavailable phosphorus was calculated by using a pore water diffusion model method. Based on the concentration gradient of deposit interstitial water and overlying water, the emission flux of bioavailable phosphorus of the sediment was calculated according to Fick's first law.

Calculation formula: $F = \varphi \cdot D_S (\partial c / \partial Z)_{Z=0}$ wherein F is the diffusion flux of molecules at the deposit-water interface, $mg \cdot (m^2 \cdot d)^{-1}$;

$\varphi$ is the porosity of the deposit, %;

$D_S$ is the actual diffusion coefficient of the molecules, $cm^2 \cdot s^{-1}$;

$(\partial c / \partial Z)_{Z=0}$ is the concentration gradient of the molecules at the deposit-water interface, $mg \cdot (L \cdot cm)^{-1}$; and the empirical relationship between $D_S$ and $\varphi$ is $D_S = \varphi^2 Do$ ($\varphi \leq 0.7$), $D_S = \varphi Do$ ($\varphi > 0.7$).

As shown in FIG. 2, at step S13, dewatering treatment was performed on the sediment to be governed on the basis of the determined position and depth of the sediment to be governed in step S11 and step S12:

firstly using nitrate to adjust pH of a water body of an area to be governed to 7.5-8.3, and changing dominant flora in the sediment in cooperation with low-oxygen aeration of 50 mg/L; and then placing the sediment to be governed in a low-voltage high-current electric field with a voltage of 12 V and a current of 10 A, and performing dewatering treatment on the sediment under vacuum negative pressure conditions.

After the nitrate was added, the dominant flora in the sediment was transformed from Clostridia to Gamma-proteobacteria at the class level, its relative abundance could reach 60.0%, and anaerobic florae such as sulfobacteria was effectively inhibited. Denitrifying florae such as *Rhodanobacter*, *Thiobacillus* and *Thermomonas* appeared at the genus level, thereby creating a good and stable habitat for the ecosystem at the bottom of the water body and realizing the objective of regulating intercellular water in the sediment.

A carbon fiber bundle with excellent conductivity used as a conductive current collector and conductive carbon black and graphite powder used as key conductive materials were blended with plastic and thermoformed to prepare a novel electrode material whose conductivity and mechanical properties all satisfied electrodynamic dewatering, thereby solving the problems of high price and poor mechanical properties in the traditional electrode materials (such as precious metal coated electrodes and graphite).

After the treatment, the water content of the sediment is reduced to about 50%, and the volume of the sediment is reduced by 20-30%. Then, there is no need to perform ion exchange membrane treatment on the dewatered sludge. Compared with the traditional sediment dewatering technology, the dewatering cost and the subsequent treatment cost of electrodynamic sludge dewatering are reduced by 30% or above and about 40% respectively. After the governance, the water quality is significantly improved, reaching Class III according to the standards for surface water.

Figure 3:
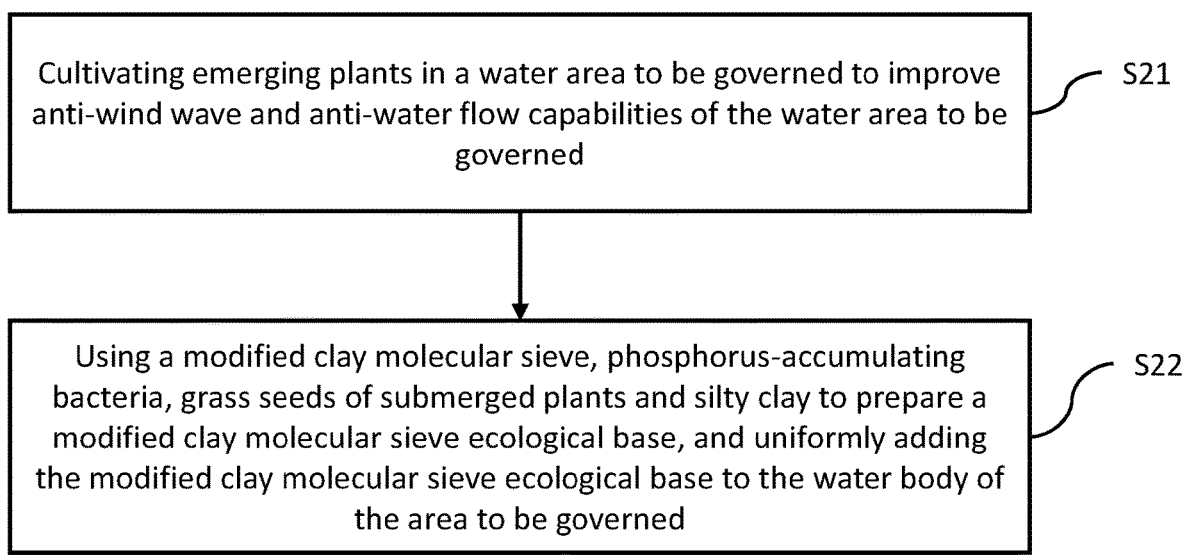
FIG. 3 is a flow chart illustrating an example method for performing S2 of FIG. 1.

Referring to FIG. 1, at step S2, a submerged vegetation system was established in a eutrophic water body to regulate primary productivity in the water body and inhibit the recovery of the algae:

As shown in FIG. 3, at S21, emerging plants were cultivated in a water area to be governed to improve anti-wind wave and anti-water flow capabilities of the water area to be governed. The cultivation density of the emerging plants was 5-6 plants/m$^2$, and the emerging plants were respectively selected from one or more of *Pontederia cordata*, *Typha orientalis* and *Canna indica* and one or more of native organisms.

As shown in FIG. 3, at S22, a modified clay molecular sieve, phosphorus-accumulating bacteria, grass seeds of submerged plants and silty clay were used to prepare a modified clay molecular sieve ecological base, and the modified clay molecular sieve ecological base was uniformly added to the water body of the area to be governed.

The preparation method of the modified clay molecular sieve ecological base included: weighing the modified clay molecular sieve and the silty clay in a ratio of 1:1, adding the grass seeds and the phosphorus-accumulating bacteria, and uniformly mixing the mixture.

The addition amount of the grass seeds was 40-60 seeds/m$^2$, and the grass seeds were *Potamogeton crispus* seeds and *Vallisneria spiralis* seeds in a number ratio of 2:1. The addition amount of the phosphorus-accumulating bacteria was 50% (v/v) relative to the total volume of the modified clay molecular sieve and the silty clay.

A preparation method of the modified clay molecular sieve included: selecting water body sediment and shore clay, and using the clay after drying, grinding and sieving, or purchasing a professional clay sewage treatment agent; and adding the treated clay to a chitosan solution to form a slurry, or spraying the chitosan solution on the constantly stirred clay (referring to CN 102502969A), where the amount of the chitosan was 1%-1.5% (w/w) of the clay.

The phosphorus-accumulating bacteria were commercially available products, for example, anaerobic phosphorus-accumulating bacteria that can be purchased from Yangzhou Haicheng Biotechnology Co., Ltd. The product was in the form of bacterial powder, and the content of the phosphorus-accumulating bacteria was up to 95% or above.

The first addition amount of the modified clay molecular sieve ecological base was not less than 500 g/m$^2$. The modified clay molecular sieve ecological base was supplementally added every 5-7 days after the first addition, and the supplemental addition amount was 50% of the first addition amount.

Figure 4:
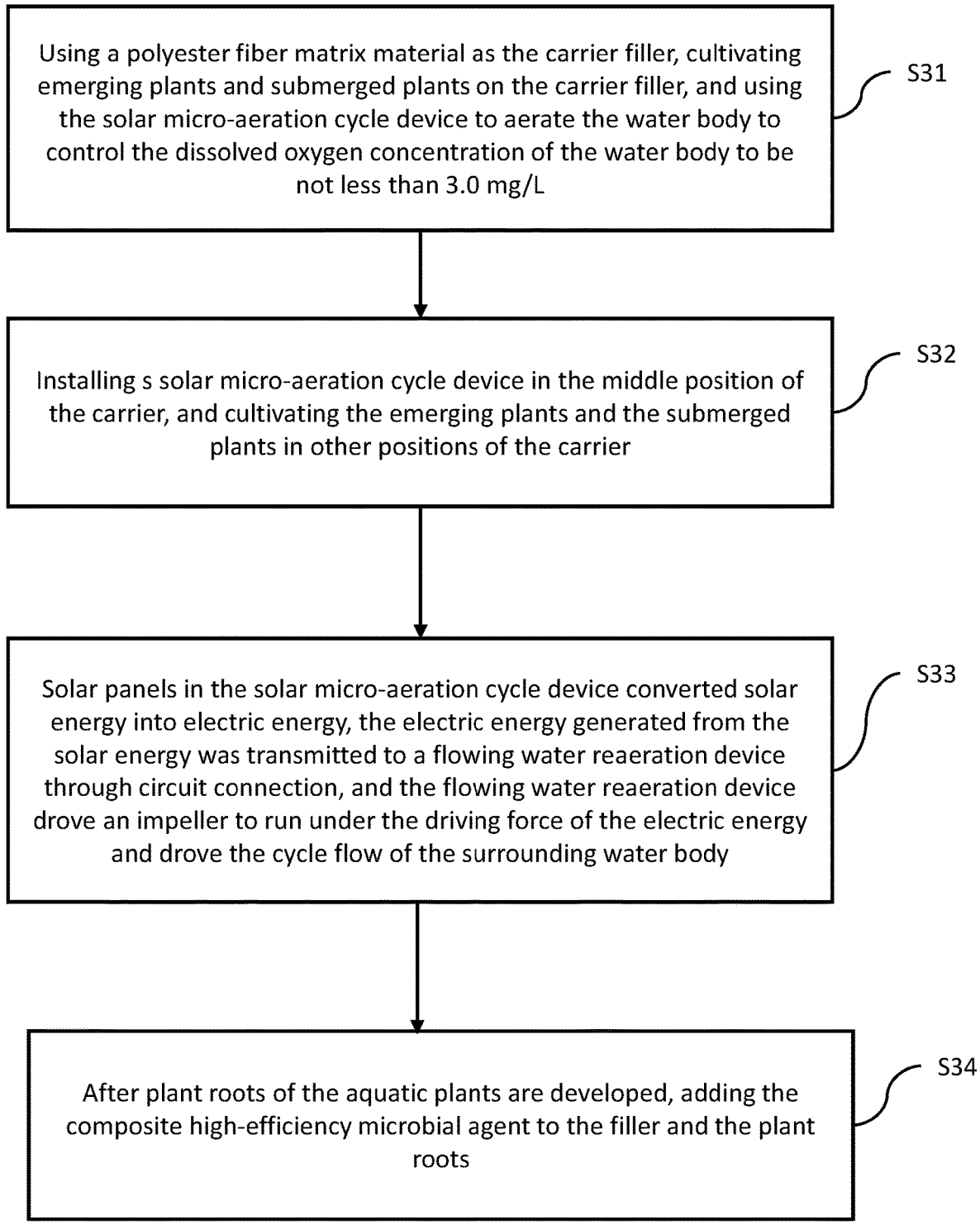
FIG. 4 is a flow chart illustrating an example method for performing S3 of FIG. 1.

Referring to FIG. 1, at step S3, a micropower biological-ecological coupled purification system was used to enhance the dissolved oxygen level in an air-water interface and the water body, enhance and activate biological reactions in the air-water interface and the water body, reduce nitrogen and phosphorus nutrients in the air-water interface and the water body and control reproduction and growth of the algae:

As shown in FIG. 4, at step S31, a polyester fiber matrix material having a specific surface area of 1:1000 and a porosity of 97% was used as a carrier filler, thereby providing a carrier for adherence of microorganisms and cultivation of emerging plants and submerged plants. In addition, the carrier filler can promote the root division and growth of aquatic plants and the seed drop and growth of wild plants, enhance the viability of plants and expand the range of plant roots.

As shown in FIG. 4, at step S32, a solar micro-aeration cycle device was installed in the middle position of the carrier, the emerging plants and the submerged plants were cultivated in other positions of the carrier. The cultivation density of the emerging plants was 5-6 plants/m$^2$, and the emerging plants may be respectively selected from one or more of *Pontederia cordata*, *Typha orientalis* and *Canna indica* and one or more of native organisms. The cultivation density of the submerged plants was 40-60 plants/m$^2$, and the submerged plants may be selected from *Elodea nuttallii* (preferred in cold seasons) and *Vallisneria spiralis* (preferred in warm seasons). The formed micropower biological-ecological coupled purification system was placed in the water body of 0.5 m or above.

As shown in FIG. 4, at step S33, solar panels in the solar micro-aeration cycle device converted solar energy into electric energy, the electric energy generated from the solar energy was transmitted to a flowing water reaeration device through circuit connection, and the flowing water reaeration device drove an impeller to run under the driving force of the electric energy and drove the cycle flow of the surrounding water body, thereby creating a suitable aerobic environment for the surrounding area, and enhancing the dissolved oxygen level of the water body by not less than 3.0 mg/L. The output power of the electric energy was 100 w-20 kw, the cycle flux driving the cycle flow of the water body was 100-50000 m$^3$/h, and the flowing water distance or action range was 100-3500 m.

As shown in FIG. 4, at step S34, after the plant roots of the micropower biological-ecological coupled purification system were developed, a composite high-efficiency microbial agent was added to the filler and the plant roots. The microbial agent was mainly extracted and domesticated from nature, and had the feature of efficiently decomposing organic matter, ammonia nitrogen, total nitrogen and other pollutants.

After the system ran for 2 months, the density of cyanobacteria and the germination rate of the submerged plants in water were tested.

A phytoplankton net was used to take a phytoplankton sample, the density of cyanobacteria was counted with a microscope, and at the same time, submerged plant seedlings were counted to calculate the germination rate of seeds.

The results showed that the number of cyanobacteria was reduced by about 60% as compared with the case with no treatment, and the seed germination rate of the submerged plants reached 82.5%.

Only specific implementations of the present disclosure are described above, so that those skilled in the art can understand or realize the present disclosure. Various modifications to these embodiments will be obvious to those skilled in the art, and the general principles defined herein can be realized in other embodiments without departing from the spirit or scope of the present disclosure. Therefore, the present disclosure will not be limited to the embodiments described herein, but must conform to the widest scope consistent with the principles and novel characteristics disclosed herein.

The invention claimed is:

1. A method for water environment multi-interface governance and restoration in river and lake, comprising:
performing an accurate locating and in-situ treatment on pollutants at a sediment-water interface to control an emission of sediment nutritive salts and a dormancy and recovery of algae;
establishing a submerged vegetation system in a eutrophic water body to regulate primary productivity in the eutrophic water body and inhibit the recovery of the algae, comprising:
cultivating emerging plants in a water area to be governed to improve anti-wind wave and anti-water flow capabilities of the water area to be governed; and
preparing a modified clay molecular sieve ecological base using a modified clay molecular sieve, phosphorus-accumulating bacteria, grass seeds of submerged plants, and silty clay by weighing the modified clay molecular sieve and the silty clay in a ratio of 1:1, adding the grass seeds and the phosphorus-accumulating bacteria, and uniformly mixing the mixture of the modified clay molecular sieve, the silty clay, the grass seeds, and the phosphorus-accumulating bacteria, wherein the modified clay molecular sieve is obtained by electing water body sediment and shore clay, and obtaining treated clay after drying, grinding and sieving the elected water body sediment and shore clay; and adding the treated clay to a chitosan solution to form a slurry, wherein the amount of the chitosan solution is 1%-1.5% of the treated clay; and
uniformly adding the modified clay molecular sieve ecological base to the eutrophic water body of the area to be governed; and
using a micropower biological-ecological coupled purification system to enhance a dissolved oxygen level in an air-water interface and the eutrophic water body, enhance and activate biological reactions in the air-water interface and the eutrophic water body, reduce nitrogen and phosphorus nutrients in the air-water interface and the eutrophic water body, and control reproduction and growth of the algae, comprising:
using a polyester fiber matrix material as a carrier filler, cultivating emerging plants and submerged plants on the carrier filler, and using a solar micro-aeration cycle device to aerate the eutrophic water body to control a dissolved oxygen concentration of the eutrophic water body to be not less than 3.0 mg/L; and
after plant roots of aquatic plants are developed, adding a composite high-efficiency microbial agent to the carrier filler and the plant roots.

2. The method according to claim 1, wherein a high-throughput sequencing technology and a pollutant source apportionment technology are firstly used to perform the accurate locating on a sediment to be governed, and then an electrodialysis-vacuum negative pressure dewatering technology is used to perform in-situ dewatering treatment on the sediment to be governed.

3. The method according to claim 2, wherein performing the accurate locating and in-situ treatment further comprises:
taking sediment samples at different positions of the sediment-water interface in a river/lake water area to be governed, extracting microbial DNA in the sediment samples, performing 16sRNA high-throughput sequencing analysis to obtain abundance of alkaline phosphatase phoD functional flora in the sediment samples at the different positions, and determining a sampling position of the sediment sample with the abundance of alkaline phosphatase phoD functional flora of greater than 25% as a determined position of the sediment to be governed;
measuring an emission flux of bioavailable phosphorus of the sediment at different depths at the determined position of the sediment to be governed, and determining a depth range where the emission flux is greater than 0.6 mg/L as a depth of the sediment to be governed; and
performing dewatering treatment on the sediment to be governed on a basis of the determined position and the depth of the sediment to be governed further comprising:
firstly using nitrate to adjust pH of a water body of an area to be governed to 7.5-8.3, and changing dominant flora in the sediment in cooperation with low-oxygen aeration; and then placing the sediment to be governed in a low-voltage high-current electric field, and performing dewatering treatment on the sediment under vacuum negative pressure conditions.

4. The method according to claim 1, wherein the grass seeds of the submerged plants comprise grass seeds of *Potamogeton crispus* and *Vallisneria spiralis*.

5. The method according to claim 1, wherein the micropower biological-ecological coupled purification system comprises the solar micro-aeration cycle device, the composite high-efficiency microbial agent, the carrier filler and aquatic plants cultivated thereon.

6. The method according to claim 1, wherein the polyester fiber matrix material has a specific surface area of 1:1000 and a porosity of 96-98%.

7. The method according to claim 1, wherein the solar micro-aeration cycle device comprises solar panels and a flowing water reaeration device; wherein the solar panels are located at an upper part of the device and used to supply energy to the flowing water reaeration device at a lower part at an output power of 100 w-20 kw, and the flowing water reaeration device is located at the lower part of the device, provided with an impeller, and driven by electric energy of the solar panels to promote the cycle of the eutrophic water body and drive the micropower biological-ecological coupled purification system to move.

\* \* \* \* \*